(12) United States Patent
Kopperschmidt

(10) Patent No.: US 8,715,215 B2
(45) Date of Patent: May 6, 2014

(54) METHOD FOR VERIFYING AND/OR MONITORING THE CORRECT FUNCTION OF A SUPPLY DEVICE

(75) Inventor: Pascal Kopperschmidt, Dittelbrunn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 796 days.

(21) Appl. No.: 12/733,702

(22) PCT Filed: Aug. 26, 2008

(86) PCT No.: PCT/EP2008/006990
§ 371 (c)(1),
(2), (4) Date: Mar. 16, 2010

(87) PCT Pub. No.: WO2009/036866
PCT Pub. Date: Mar. 26, 2009

(65) Prior Publication Data
US 2010/0204633 A1 Aug. 12, 2010

(30) Foreign Application Priority Data
Sep. 18, 2007 (DE) .......................... 10 2007 044 413

(51) Int. Cl.
*A61M 37/00* (2006.01)
*C02F 1/44* (2006.01)

(52) U.S. Cl.
USPC .......................... 604/6.11; 604/5.04; 210/741

(58) Field of Classification Search
USPC ............... 604/4.01, 5.01, 6.07, 6.11; 210/741
See application file for complete search history.

(56) References Cited

U.S. PATENT DOCUMENTS

| | | | |
|---|---|---|---|
| 5,429,486 A * | 7/1995 | Schock et al. | 417/476 |
| 5,928,180 A | 7/1999 | Krivitski et al. | |
| 7,674,236 B2 | 3/2010 | Daniel et al. | |
| 2005/0065459 A1 * | 3/2005 | Zhang et al. | 604/4.01 |
| 2006/0254982 A1 | 11/2006 | Kopperschmidt | |
| 2007/0058412 A1 | 3/2007 | Wang et al. | |

FOREIGN PATENT DOCUMENTS

| | | |
|---|---|---|
| DE | 101 59 620 C1 | 8/2003 |
| DE | 102 13 179 C1 | 8/2003 |
| DE | 10 2004 023 080 A1 | 12/2005 |
| DE | 10 2005 001 051 A1 | 7/2006 |
| DE | 10 2006 042 336 A1 | 3/2008 |
| EP | 0328162 A2 * | 10/1984 |
| EP | 0 328 162 A2 | 8/1989 |
| JP | 2005-511151 | 4/2005 |
| WO | WO 03/047656 | 6/2003 |
| WO | WO 2007/012915 A1 | 2/2007 |
| WO | WO 2007012915 A1 * | 2/2007 |
| WO | WO 2008/028653 A2 | 3/2008 |

OTHER PUBLICATIONS

English translation of DE 102004023080.*

* cited by examiner

*Primary Examiner* — Leslie Deak
(74) *Attorney, Agent, or Firm* — Jacobson Holman PLLC

(57) ABSTRACT

A method of checking and/or monitoring the correct operation of an adding device of a medical apparatus includes detecting a characteristic signal course being generated by the adding device. The medical apparatus includes an extracorporeal circuit with which the adding device is connected such that an agent can be introduced into the extracorporeal circuit via the adding device. The pressure loss in the extracorporeal circuit is measured and evaluated for checking and/or monitoring the correct operation of the adding device. The adding device for this purpose generates an oscillating pressure course.

33 Claims, 2 Drawing Sheets

METHOD FOR VERIFYING AND/OR MONITORING THE CORRECT FUNCTION OF A SUPPLY DEVICE

CROSS-REFERENCE TO RELATED APPLICATION

This is a national stage of PCT/EP08/006,990 filed Aug. 26, 2008 and published in German, which has a priority of German no. 10 2007 044 413.5 filed September 2007, hereby incorporated by reference.

BACKGROUND OF THE INVENTION

1. Field of Invention

The present invention relates to a method for checking and/or monitoring the correct operation of an adding device of a medical apparatus, the medical apparatus including an extracorporeal circuit with which the adding device is connected such that an agent can be introduced into the extracorporeal circuit by means of the adding device.

2. Description of the Prior Art

In particular, the medical apparatus can be a dialysis machine, in which—as also in other extracorporeal methods—an anticoagulant such as heparin or citrate must be added to the blood. For this purpose, the medical apparatus includes an adding device, usually in the form of a syringe pump, which contains the agent to be added. Before commencement of the treatment, the adding device is connected with the extracorporeal circuit, i.e. with an extracorporeal set of tubes.

In the case of syringe pumps, a syringe with the agent initially is inserted in the syringe pump and connected with the extracorporeal circuit. For adding the agent from the syringe into the extracorporeal circuit, a tappet is provided, which presses the syringe plunger into the syringe. For this purpose, the tappet is moved correspondingly via a spindle and a spindle drive. Monitoring the dose administered by such adding device is effected e.g. during the dialysis treatment by measuring the tappet displacement, e.g. by scanning by means of a resistance path. The distance covered by the delivery tappet and hence the quantity added thus can be calculated.

In this way, however, the correct addition merely is checked on the side of the syringe pump, whereas it is not ensured whether the quantity of anticoagulant to be infused actually arrives in the extracorporeal circuit. In known machines, it is also checked initially at the beginning of the treatment whether the syringe pump is correctly connected. During the time of the treatment, however, a disconnection or other malfunction could not be detected automatically.

In particular in the case of an incorrectly inserted infusion syringe, an initial coupling test could be terminated successfully. Problems resulting from the incorrectly inserted infusion syringe, which only arise during the treatment and lead to a deviation of the prescribed infusion dose, might, however, not be detected as the administered infusion dose merely is monitored indirectly via the tappet movement, but not directly via the plunger movement.

SUMMARY OF THE INVENTION

Therefore, it is the object of the present invention to provide an improved method for checking and/or monitoring the correct operation of an adding device. In particular, this method should provide for directly checking the correct operation of the adding device also during the ongoing operation.

In accordance with the invention, this object is solved by a method as described herein. In this method, a characteristic signal course is detected in the extracorporeal circuit, with the adding device generating the characteristic signal course. Advantageously, a signal course is measured in the extracorporeal blood circuit and evaluated for checking and/or monitoring the correct operation of the adding device. A characteristic signal course is detected when the adding device operates correctly and generates the same, thus enabling a direct checking and/or monitoring. By checking whether a characteristic signal course actually exists, it can directly be monitored whether the adding device operates correctly. If the adding device is, however, not coupled correctly or if there are any other problems which prevent the correct addition of fluid from the adding device into the extracorporeal circuit, a characteristic signal course will not be generated in the same, so that the malfunction of the adding device can be detected reliably. As a result, it no longer is necessary to fall back on the indirect check, e.g. by the tappet movement of a syringe pump, but the correct operation can be measured directly. In particular, the characteristic signal course also can be generated and detected during the ongoing operation of the medical apparatus, so that the method of the invention provides for monitoring continuously.

Advantageously, the characteristic signal course is a characteristic pressure course. The adding device here generates the characteristic pressure course in the extracorporeal circuit, which can then be detected for checking and/or monitoring the correct operation of the adding device. This provides for easily checking and/or monitoring e.g. via a pressure sensor in the extracorporeal circuit.

Alternatively, it is likewise conceivable that the characteristic signal course is detected in the electrical parameters, in particular in the drive current of a pump arranged in the extracorporeal circuit, which pumps fluid through the extracorporeal circuit. In these electrical parameters, there can also be detected a characteristic signal which is generated by means of the adding device. A characteristic pressure course generated by the adding device no longer would be measured directly, but detected indirectly as a characteristic signal course in the electrical parameters of the pump arranged in the extracorporeal circuit.

Furthermore, the characteristic signal course of the invention advantageously includes a repeated alternating rise and fall of the signal, in particular a plurality of successive pulse-shaped signals. In this way, the checking and/or monitoring of the correct operation of the adding device can be ensured safely and reliably. In particular, such characteristic signal course also provides for monitoring the correct operation of the adding device, while the medical apparatus is in operation and the extracorporeal circuit correspondingly is open, so that an individual signal might not safely be detected.

Furthermore, the characteristic signal course advantageously includes an oscillating course. By means of such oscillating signal course, the characteristic signal can be detected safely and easily. Such oscillating signal course, in particular an oscillating pressure course, can particularly easily be generated by the adding device and in particular can also be detected easily when the region in which the adding device introduces some agent into the extracorporeal circuit is not closed, but open, e.g. during operation of the medical device.

The characteristic, advantageously oscillating signal course with a correct operation of the adding device advantageously is based on the fact that the rate of delivery of the adding device varies in time. It is conceivable, for instance, that the addition is clocked, which can lead to corresponding pressure fluctuations in the extracorporeal circuit. In particular when only very small amounts of fluid should be infused, a clocked addition usually is not sufficient, however, to generate a measurably oscillating signal course, e.g. in the form of an oscillating pressure course, by means of which the correct operation of the adding device might reliably be detected.

Advantageously, the characteristic signal course therefore is generated by a corresponding, in particular repeated, in particular oscillating actuation of the adding device, by means of which fluid alternately is added to and withdrawn from the extracorporeal blood circuit. In this way, a clear characteristic signal can be generated, which can reliably be detected.

Advantageously, the volumes moved during the in particular repeated, in particular oscillating actuation of the adding device are less than one milliliter. It can thus be ensured that the fluctuations in the concentration of the agent added are minimized. Nevertheless, oscillating pressure fluctuations thereby can be generated, which can clearly be detected in the pressure signal.

In a furthermore advantageous way, a corresponding characteristic, in particular oscillating movement is superimposed on a continuous movement of the adding device, by means of which the agent is added into the extracorporeal circuit, for generating the characteristic, in particular oscillating signal course. Thus, if a characteristic signal course is detected in the extracorporeal blood circuit, this means that the adding device is correctly coupled to the extracorporeal circuit and operates correctly, so that the fluid added by the continuous movement of the adding device actually arrives in the extracorporeal circuit. On the other hand, if no characteristic signal course is detected, this means that no fluid is added.

In a furthermore advantageous way, the signal course additionally is measured over several pulses, in particular over several periods of the oscillation, in order to check or monitor the correct operation of the adding device. This provides for a reliable detection of the characteristic signal course such as an oscillation in the pressure course. Furthermore, the oscillation advantageously is effected with a period which is at least constant for a certain time in accordance with the invention.

Furthermore, the characteristic, in particular oscillating signal course advantageously is detected in the signal of a pressure sensor in accordance with the invention. A characteristic pressure course thus can be detected directly and easily, in order to check and/or monitor the correct operation of the adding device.

Alternatively, the characteristic, in particular oscillating signal course also can be detected in the electrical parameters, in particular in the drive current, of a pump arranged in the extracorporeal circuit, which pumps fluid through the extracorporeal circuit. In this way, a characteristic signal course also can reliably be detected, and a pressure sensor possibly can be omitted. In the case of a change in pressure—caused by the changed signal course through the adding device—upstream or downstream of the pump in the extracorporeal circuit, the same must be operated e.g. with a higher or lower current. This change in power consumption can be detected and can be evaluated in connection with the feeding of the characteristic signal course. In a case of error (infusion line not connected correctly or syringe wrongly inserted), no characteristic signal course will be detected correspondingly.

Furthermore, the characteristic, in particular oscillating signal course advantageously is detected by means of a signal analysis, in particular by means of a frequency analysis. A frequency analysis can be effected e.g. by known methods such as a Fourier transformation.

In the method of the invention, the actuation of the adding device on the whole advantageously leads to an addition of the agent into the extracorporeal circuit. The determination of the added quantity of the agent on a time average of the movement of the adding device furthermore can be effected as in the prior art via a transducer on the adding device, by means of whose measured values the added quantity is determined indirectly. The fact that this quantity actually has arrived in the extracorporeal circuit is, however, detected in accordance with the invention via the characteristic signal course, such as an oscillating pressure course.

Advantageously, the monitoring of the correct operation of the adding device in accordance with the invention continuously is effected during the addition of the agent into the extracorporeal circuit. Such permanent monitoring is possible due to the characteristic and in particular oscillating signal course, such as an oscillating pressure course, which also can be generated and detected during the ongoing operation of the medical apparatus.

In a furthermore advantageous way, checking and/or monitoring the adding device is effected while fluid flows through the extracorporeal circuit, in particular while fluid is pumped through the extracorporeal circuit by means of a pump arranged in the same. Such checking or monitoring has not been possible with known methods.

In an advantageous way, checking and/or monitoring the adding device is effected during the ongoing operation of the medical apparatus. During the therapy, safety can be increased considerably, as now a direct monitoring for the first time is possible during the ongoing operation.

Advantageously, the operation of the medical apparatus is interrupted and/or a warning signal is generated, when a malfunction of the adding device is detected. Thus, it is ensured that errors e.g. when coupling the adding device are eliminated immediately.

Advantageously, the agent added is an anticoagulant, a drug or some other agent to be infused, which is added to the extracorporeal circuit. In a furthermore advantageous way, the anticoagulant is heparin.

In a furthermore advantageous way, the adding device of the invention is a syringe pump with a syringe inserted therein. In particular for adding anticoagulant or other drugs, which must be added in a controlled way only in very small quantities, such syringe pump is particularly useful for addition.

When using a syringe pump, the characteristic, in particular oscillating signal course advantageously is generated by a corresponding actuation of the movement of the tappet of the syringe pump.

Advantageously, a characteristic, in particular oscillating movement, which generates the characteristic signal course and thereby in particular the oscillation in the pressure course, is superimposed on the continuous translational movement of the tappet of the syringe pump by means of which the agent is added to the extracorporeal circuit.

Advantageously, the processes of the invention are controlled by means of a control device of the medical apparatus. In particular, these processes advantageously are automatically generated by the control device.

The present invention furthermore comprises a medical apparatus, preferably a dialysis machine, suitable for accommodation of an extracorporeal circuit, with an adding device connectable with the extracorporeal circuit such that an agent can be introduced into the extracorporeal circuit by means of the adding device. In accordance with the invention, this medical apparatus includes a control device which actuates the adding device such that the same generates a characteristic signal course in the extracorporeal circuit, the characteristic signal course being detected in the process. Quite obviously, such medical apparatus provides the same advantages, in particular in terms of operating safety, as described above with respect to the method.

Advantageously, the control evaluates a signal course, in particular a signal course in the extracorporeal circuit. By means of this evaluation of the signal course, a characteristic signal course as it is advantageously generated by the control via the actuation of the adding device can be detected, in order to check and/or monitor the correct operation of the adding device.

Furthermore, the control of the medical apparatus in accordance with the invention advantageously is configured such that it performs one of the methods of the invention as described above. In particular, the control advantageously performs one of these methods automatically.

Advantageously, the adding device of the medical apparatus is a syringe pump in which a syringe can be inserted, so that the plunger of the syringe can be moved via a tappet. The control generates a characteristic, in particular oscillating movement of the tappet. When the syringe is correctly inserted and connected, this movement of the tappet generates a corresponding characteristic, in particular oscillating movement of the syringe plunger, which in turn produces a characteristic signal course, in particular an oscillating pressure course in the extracorporeal circuit. By measuring this characteristic signal course or pressure course, the correct operation of the syringe pump can be monitored, which in turn is effected automatically via the control.

Advantageously, the movement of the tappet is measured in addition to the check effected by the method of the invention, which directly monitors the correct operation of the addition via the syringe. Via this movement of the tappet, the infused quantity then is calculated, as is known from the prior art. For this purpose, the syringe pump advantageously includes a corresponding transducer, e.g. a resistance path.

In a furthermore advantageous way, the medical apparatus includes a pressure sensor for measuring the pressure course in the extracorporeal circuit. In particular, this pressure sensor can be a pressure sensor anyhow provided in the medical apparatus, e.g. the arterial pressure measurement unit.

In a furthermore advantageous way, the medical apparatus includes a pump for the transport of fluids in the extracorporeal blood circuit.

In a furthermore advantageous way, the adding device can be connected with the arterial line of a set of blood tubes for an extracorporeal method of blood treatment. Here, there is usually also provided the arterial pressure measurement unit, so that for performing the method of the invention, the control of the medical apparatus merely must be adapted correspondingly, but otherwise no constructive changes will have to be made.

Advantageously, the medical apparatus of the invention is a medical apparatus for dialysis, hemodialysis, hemofiltration, hemodiafiltration, for adsorptive blood cleaning, in a transfusion method or in an autotransfusion method. In all these medical apparatuses, the monitoring and/or checking of the correct operation of the adding device in accordance with the invention can considerably increase the safety of the treatment.

In a furthermore advantageous way, the present invention therefore comprises the use of a medical apparatus in accordance with the invention in dialysis, hemodialysis, hemofiltration, hemodiafiltration, for absorptive blood cleaning, in a transfusion method or in an autotransfusion method.

The present invention furthermore comprises an adding device, in particular a syringe pump for adding a medical fluid into a line, in particular into an extracorporeal circuit or an infusion tube. In accordance with the invention, this adding device includes a control which actuates the adding device such that the same generates a characteristic signal course in the line, with means for detecting the characteristic signal course being provided. Thus, the adding device of the invention with the corresponding control for monitoring and/or checking the correct operation of the adding device also can be used to great advantage independent of the medical apparatus in accordance with the invention. For instance, the adding device can also be used for monitoring an infusion.

BRIEF DESCRIPTION OF THE DRAWINGS

Advantageously, the adding device or the control of the adding device is configured such that it performs one of the methods described above.

The present invention will now be explained in detail with reference to an embodiment and the drawings, in which.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
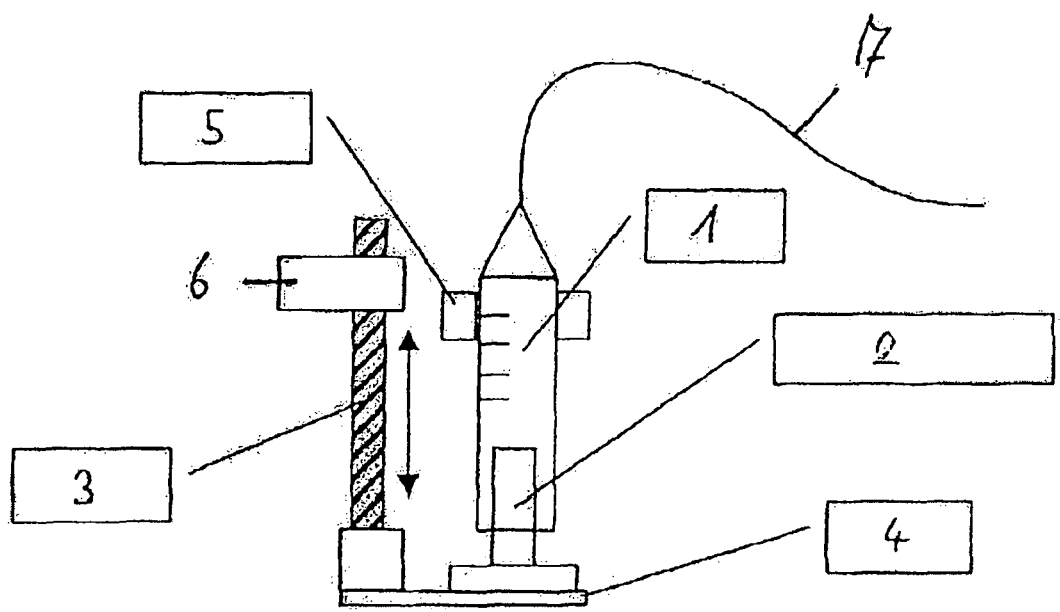
FIG. 1: shows an embodiment of an adding device in accordance with the invention.

FIG. 1 shows an embodiment of an adding device in accordance with the invention, in this case a syringe pump. In such syringe pump, a syringe 1 is inserted in a holder 5, so that the syringe plunger 2 of the syringe 1 can be moved via the tappet 4. The syringe plunger 2 is connected with the tappet 4 such that the syringe plunger can both be pressed into the syringe and be withdrawn from the syringe. The tappet 4 itself is reciprocated via a spindle 3, which is driven via a spindle drive 6. For scanning the tappet movement, there is also provided a non-illustrated resistance path, so that by measuring the distance covered by the delivery tappet, the discharge of volume by the syringe 1 can be determined.

The adding device of the invention is part of a medical apparatus in accordance with the invention, in particular a dialysis machine. In this medical apparatus, an extracorporeal circuit can be inserted, in particular in the form of a set of blood tubes. Upon insertion, the syringe 1 then is connected with the extracorporeal circuit via a line 7, e.g. with the arterial line of the set of blood tubes. Via the syringe pump, anticoagulant such as heparin or citrate, which is charged to the syringe 1, thus can continuously be added to the blood flowing through the extracorporeal circuit.

The control of the medical apparatus in accordance with the invention is designed such that at first, before commencement of the treatment, the correct coupling of the syringe to the extracorporeal circuit initially is checked. This can already be effected by the method of the invention, alternative methods also being possible at the beginning of the treatment.

For continuously monitoring the correct operation of the adding device, the method of the invention now is automatically performed in the medical apparatus in accordance with the invention via the control. For this purpose, a characteristic movement, which in this embodiment is oscillating, is superimposed on the continuous movement of the tappet 4 for continuous infusion. When all components operate correctly, this oscillating movement of the tappet generates an oscillating pressure course in the extracorporeal circuit. The amplitude of the pressure oscillation depends on the system compliance and on the magnitude of the tappet movement. The volumes moved during the oscillation are less than one milliliter and thus only produce minimum fluctuations in the concentration of the agent added in the extracorporeal circuit, but nevertheless lead to easily measurable and detectable pressure fluctuations. For monitoring the function of the adding device, the pressure in the extracorporeal circuit now is measured by means of a pressure sensor e.g. in the arterial line and evaluated correspondingly. With a known period of oscillation, the identification of the oscillation in the pressure course is feasible by means of a usual signal analysis. There can be used in particular a frequency analysis, e.g. via a Fourier transformation.

Figure 2:
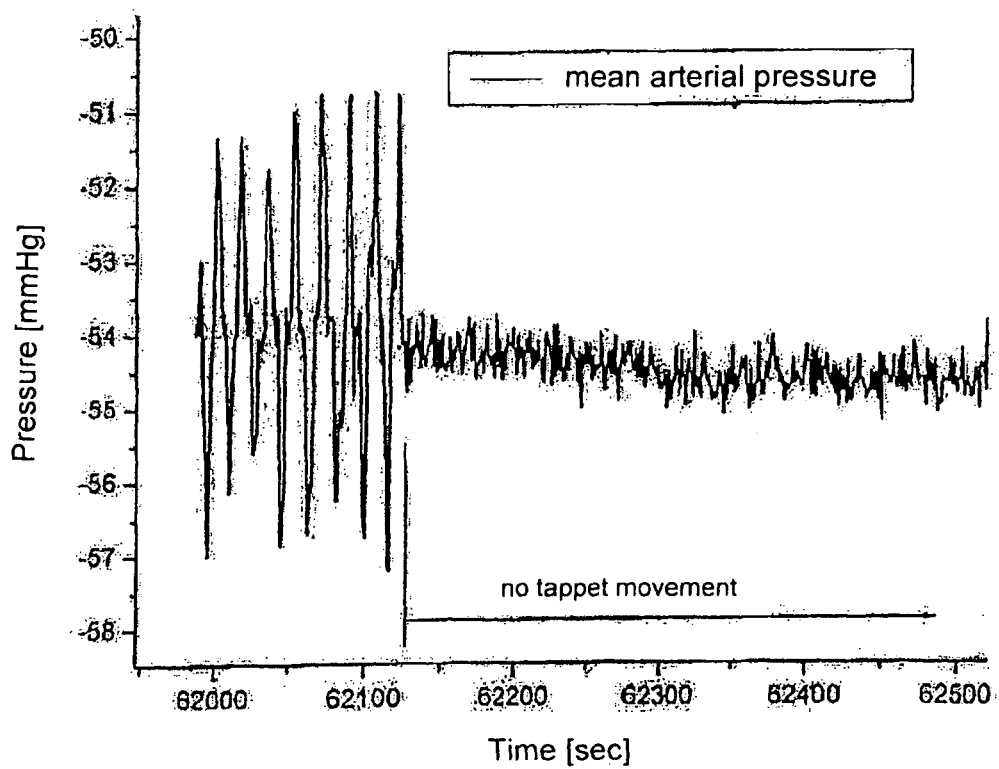
FIG. 2: shows a diagram of the pressure course during an embodiment of the method of the invention.

FIG. 2 shows such pressure course in the mean arterial pressure. In the left-hand region of the diagram, the adding device initially operates correctly, so that an oscillation can be detected in the pressure course. Such oscillation is detected via the signal analysis and enables the control of the medical apparatus to monitor the correct operation of the adding device. However, if there is an error in the operation of the adding device, as in the right-hand portion of the diagram, the pressure course is not superimposed with an oscillation. Such signal would be obtained in the case of a wrongly inserted syringe 1, where the tappet 4 would not move the syringe plunger 2. There would neither be obtained an oscillating signal in the pressure course, if there was no correct coupling between the syringe 1 and the extracorporeal circuit.

The control of the medical apparatus in accordance with the invention now detects that there is no oscillation in the pressure signal. If such lack of oscillation is detected, although the adding device is actuated, a malfunction is assumed. The control device then activates a warning function, e.g. via an optical or acoustic signal. It can thus be prevented that a malfunction of the adding device results in an insufficient addition of infusion agents. In a further embodiment or in particular cases, the control device also can stop the medical apparatus automatically.

By means of the method of the invention or by the corresponding control of the medical apparatus in accordance with the invention it is possible for the first time to check the correct operation of the adding device during operation of the medical apparatus, i.e. during the actual treatment. In particular, the pressure fluctuations in the pressure course as a result of the oscillating movements of the tappet also are obtained when fluid flows through the extracorporeal circuit, in particular also when blood is pumped through the extracorporeal circuit by means of a blood pump. Advantageously, the pressure sensor by means of which the pressure course in the extracorporeal blood circuit is measured, therefore is arranged on the same side of a blood pump as the adding device. Adding device and pressure sensor advantageously are arranged in series on the suction side of a pump in the extracorporeal circuit.

The electrical parameters of the blood pump such as its power consumption, current or voltage, which are influenced by the oscillating pressure pulses, can be used for detection and evaluation.

The continuous monitoring of the infusion rate of delivery thus on the one hand consists in ensuring the correct operation of the adding device, in particular the correct coupling between syringe 1 and tappet 4, and the correct coupling of the syringe 1 to the extracorporeal circuit by the present invention.

In addition, monitoring furthermore comprises a measurement of the infusion quantity administered within a specific time. This is realized by scanning the tappet displacement with its resistance path as in the prior art.

By ensuring the permanent coupling by means of the method of the invention, it is now possible for the first time to reliably detect problems in connection with the infusion, which only arise during the treatment and would lead to a deviation of the actually administered infusion dose from the dose measured.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of checking and/or monitoring correct operation of an adding device of a medical apparatus that includes an extracorporeal circuit with which the adding device is connected such that an agent can be introduced into the extracorporeal circuit via the adding device, said method comprising:

detecting in the extracorporeal circuit a characteristic oscillating signal course being generated by the adding device, said characteristic oscillating signal course being generated by superimposing a corresponding oscillating movement of the adding device, via which a fluid is alternately added to and withdrawn from the extracorporeal circuit, on a continuous movement of the adding device.

2. The method according to claim 1, wherein the characteristic oscillating signal course is a characteristic pressure course.

3. The method according to claim 1, wherein the characteristic oscillating signal course includes a repeated alternating rise and fall of a signal.

4. The method according to claim 3, wherein the repeated alternating rise and fall of the signal includes a plurality of successive pulse-shaped signals.

5. The method according to claim 1, wherein the characteristic oscillating signal course is generated by a corresponding, repeated, and oscillating actuation of the adding device.

6. The method according to claim 5, wherein volumes of the fluid moved during the repeated, oscillating actuation of the adding device are less than 1 ml.

7. The method according to claim 1, wherein the characteristic oscillating signal course is detected in a signal of a pressure sensor.

8. The method according to claim 1, wherein the characteristic oscillating signal course is detected in electrical parameters associated with a drive current of a pump arranged in the extracorporeal circuit for pumping fluid therethrough.

9. The method according to claim 1, wherein the characteristic oscillating signal course is detected by a frequency signal analysis.

10. The method according to claim 1, wherein actuation of the adding device leads to an addition of the agent into the extracorporeal circuit.

11. The method according to claim 1, wherein the checking and/or monitoring of the correct operation of the adding device is effected continuously during the addition of the agent into the extracorporeal circuit.

12. The method according to claim 1, wherein the checking and/or monitoring of the correct operation of the adding device is effected while the fluid flows through the extracorporeal circuit, said fluid being pumped through the extracorporeal circuit by a pump arranged therein.

13. The method according to claim 1, wherein the checking and/or monitoring of the correct operation of the adding device is effected during operation of the medical apparatus.

14. The method according to claim 1, wherein, when a malfunction of the adding device is detected, at least one of the operation of the medical apparatus being interrupted, and a warning signal being generated, occurs.

15. The method according to claim 1, wherein the agent is an anticoagulant, a drug, or another agent to be infused.

16. The method according to claim 15, wherein the anticoagulant is heparin.

17. The method according to claim 1, wherein the adding device is a syringe pump with a syringe inserted therein.

18. The method according to claim 17, wherein the characteristic oscillating signal course is generated by a corresponding actuation of movement of a tappet of the syringe pump.

19. The method according to claim 17, wherein a corresponding characteristic oscillating movement is superimposed on a continuous translational movement of a tappet of the syringe pump for generating the characteristic oscillating signal course.

20. The method according to claim 1, wherein the method of checking and/or monitoring the correct operation of the adding device is effected by a control device of the medical apparatus.

21. The method according to claim 1, wherein the medical apparatus is configured for dialysis, hemodialysis, hemofiltration, hemodiafiltration, adsorptive blood cleaning, a transfusion method, or an autotransfusion method.

22. A medical apparatus configured to accommodate an extracorporeal circuit, with an adding device connectable with the extracorporeal circuit such that via the adding device an agent can be introduced into the extracorporeal circuit, said medical apparatus comprising:
  a control element which actuates the adding device to generate a detectable characteristic oscillating signal course in the extracorporeal circuit, the characteristic oscillating signal course being generated by superimposing a corresponding oscillating movement of the adding device, via which a fluid is alternately added to and withdrawn from the extracorporeal circuit, on a continuous movement of the adding device.

23. The medical apparatus according to claim 22, wherein the control element evaluates the characteristic oscillating signal course.

24. The medical apparatus according to claim 22, further comprising a control element for detecting the characteristic oscillating signal course in the extracorporeal circuit.

25. The medical apparatus according to claim 22, wherein the adding device is a syringe pump in which a syringe is insertable, with a plunger of the syringe being movable via a tappet.

26. The medical apparatus according to claim 22, further comprising a pressure sensor for measuring a pressure course in the extracorporeal circuit.

27. The medical apparatus according to claim 22, wherein the adding device is connectable with an arterial line of a set of blood tubes for an extracorporeal method of blood treatment.

28. The medical apparatus according to claim 22, wherein the medical apparatus is configured for dialysis, hemodialysis, hemofiltration, hemodiafiltration, adsorptive blood cleaning, a transfusion method, or an autotransfusion method.

29. The medical apparatus according to claim 22, wherein the apparatus is a dialysis machine.

30. An adding device for addition of a medical fluid into a line, said adding device comprising:
  a control element which actuates the adding device to generate a characteristic oscillating signal course in the line, the characteristic oscillating signal course being generated by superimposing a corresponding oscillating movement of the adding device, via which the medical fluid is alternately added to and withdrawn from the extracorporeal circuit, on a continuous movement of the adding device; and
  an element for detecting the characteristic oscillating signal course.

31. The method according to claim 4, wherein the characteristic oscillating signal course is measured over several, of the pulse-shaped signals corresponding to several periods of the oscillation.

32. The adding device according to claim 30, wherein the adding device is a syringe pump.

33. The adding device according to claim 30, wherein the line is an element of an extracorporeal circuit, or an infusion tube.

* * * * *